United States Patent [19]

Allard

[11] Patent Number: 5,484,440
[45] Date of Patent: Jan. 16, 1996

[54] BONE SCREW AND SCREWDRIVER

[75] Inventor: Randall N. Allard, Plymouth, Ind.

[73] Assignee: Zimmer, Inc., Warsaw, Ind.

[21] Appl. No.: 292,592

[22] Filed: Aug. 18, 1994

Related U.S. Application Data

[63] Continuation of Ser. No. 970,908, Nov. 3, 1992, abandoned.

[51] Int. Cl.⁶ .......................... A61B 17/56; A61B 17/58
[52] U.S. Cl. .......................... 606/73; 606/104; 411/407; 128/898
[58] Field of Search .................... 411/407, 919; 81/451–453, 455–457; 128/898

[56] References Cited

U.S. PATENT DOCUMENTS

| | | | |
|---|---|---|---|
| 1,039,751 | 10/1912 | Ingram | 81/453 |
| 2,248,054 | 7/1941 | Becker | 606/104 X |
| 2,524,095 | 10/1950 | Williams | 81/453 |
| 2,570,465 | 10/1951 | Lundholm | 128/92 |
| 2,669,896 | 2/1954 | Clough | 81/453 X |
| 2,796,099 | 6/1957 | Dierker | 81/456 |
| 2,829,683 | 4/1958 | Mitchell et al. | 81/451 |
| 2,842,997 | 7/1958 | Wentling | 81/418 |
| 3,604,487 | 9/1971 | Gilbert | 606/104 X |
| 4,124,026 | 11/1978 | Berner et al. | 606/104 |
| 4,130,152 | 12/1978 | Bolen | 81/451 |
| 4,140,111 | 2/1979 | Morrill | 128/92 E |
| 4,236,555 | 12/1980 | Dewey | 81/451 X |
| 4,347,845 | 9/1982 | Mayfield | 128/303 R |
| 4,409,968 | 10/1983 | Drummond | 128/69 |
| 4,526,071 | 7/1985 | Post | 81/451 |
| 4,567,884 | 2/1986 | Edwards | 128/69 |
| 4,581,962 | 4/1986 | Marbourg | 81/451 |
| 4,704,929 | 11/1987 | Osada | 81/451 |
| 4,776,328 | 10/1988 | Frey et al. | 128/92 VT |
| 4,858,601 | 8/1989 | Glisson | 128/92 R |
| 4,901,712 | 2/1990 | Voegell et al. | 606/75 |
| 4,903,691 | 2/1990 | Heinl | 606/70 |
| 4,903,692 | 2/1990 | Reese | 606/99 |
| 4,911,154 | 3/1990 | Vickers | 606/104 |
| 4,936,172 | 6/1990 | Jackson | 81/451 |
| 4,963,144 | 10/1990 | Huene | 606/73 |
| 4,995,810 | 2/1991 | Söderberg | 433/141 |
| 4,997,432 | 3/1991 | Keller | 606/61 |
| 5,019,080 | 5/1991 | Hemer | 606/73 |
| 5,020,519 | 6/1991 | Hayes et al. | 128/69 |
| 5,052,253 | 10/1991 | Lin | 81/451 |
| 5,056,386 | 10/1991 | Chaconas | 81/451 |
| 5,139,499 | 8/1992 | Small et al. | 606/73 |
| 5,207,127 | 5/1993 | Nick | 81/451 X |

FOREIGN PATENT DOCUMENTS

| | | | |
|---|---|---|---|
| 2668919 | 5/1992 | France | 606/104 |
| 613730 | 12/1960 | Italy | 81/457 |

OTHER PUBLICATIONS

Danek Medical, Inc.—TSRH Screwdriver—No Date Available.
Zimmer, Inc.—Catalog pp. A87, A97, A99—1991 catalog.
Zimmer, Inc.—Catalog pp. D39,D40,C53,C54,E60,E61, E62—1987 catalog.

Primary Examiner—Mickey Yu
Assistant Examiner—Brian E. Hanlon
Attorney, Agent, or Firm—Margaret L. Geringer

[57] ABSTRACT

A bone screw screwdriver and method for securely, positively locking a bone screw to the screwdriver. The screwdriver includes an extending handle through which a drive rod is slidingly disposed. A tongue at one end of the drive rod interlocks within a groove in the bone screw. The drive rod selectively locks within the handle to positively interlock the bone screw with the screwdriver. A tab on the screwdriver engages a corresponding recess on the bone screw to prevent rotation and removal of the bone screw from the screwdriver.

4 Claims, 2 Drawing Sheets

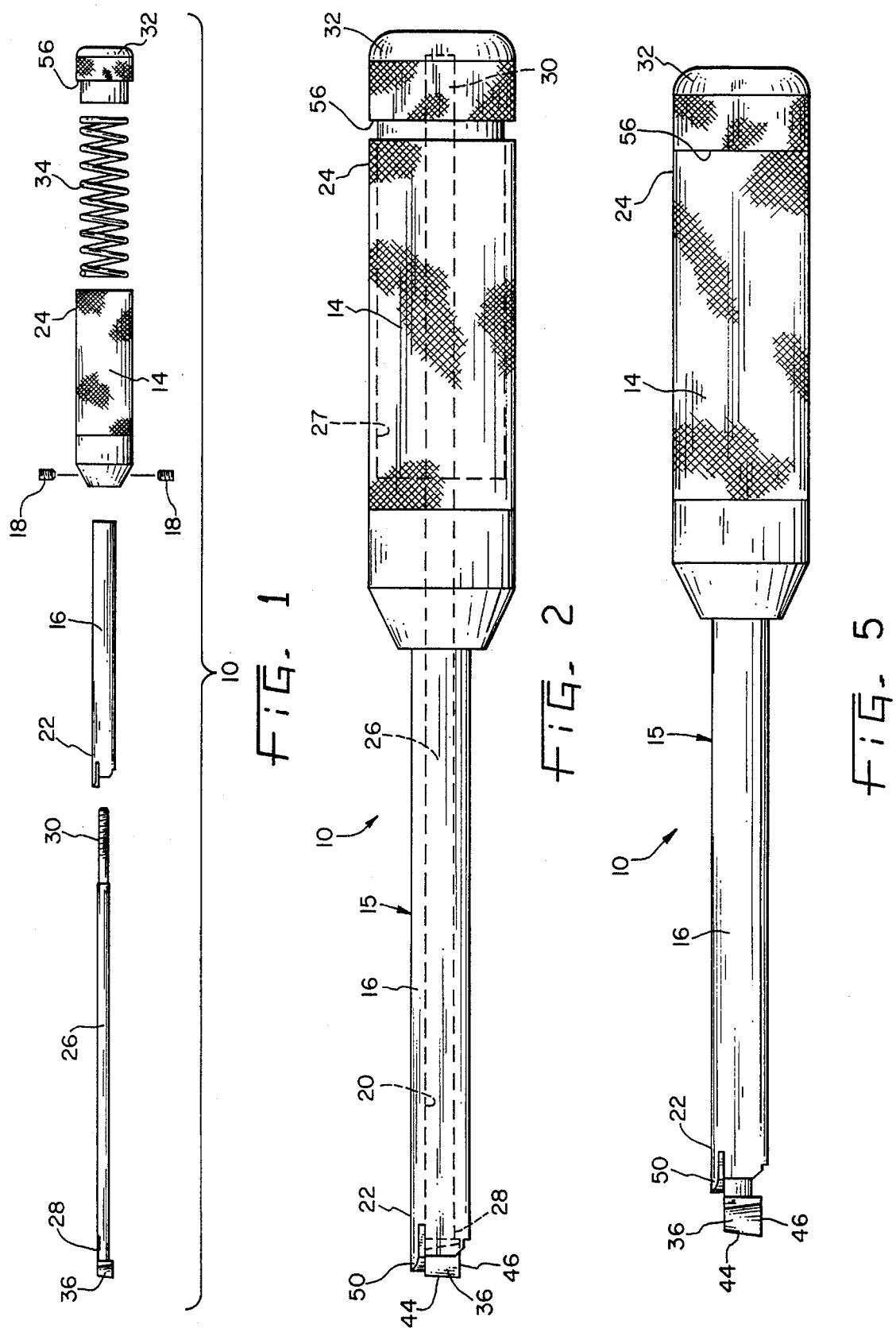

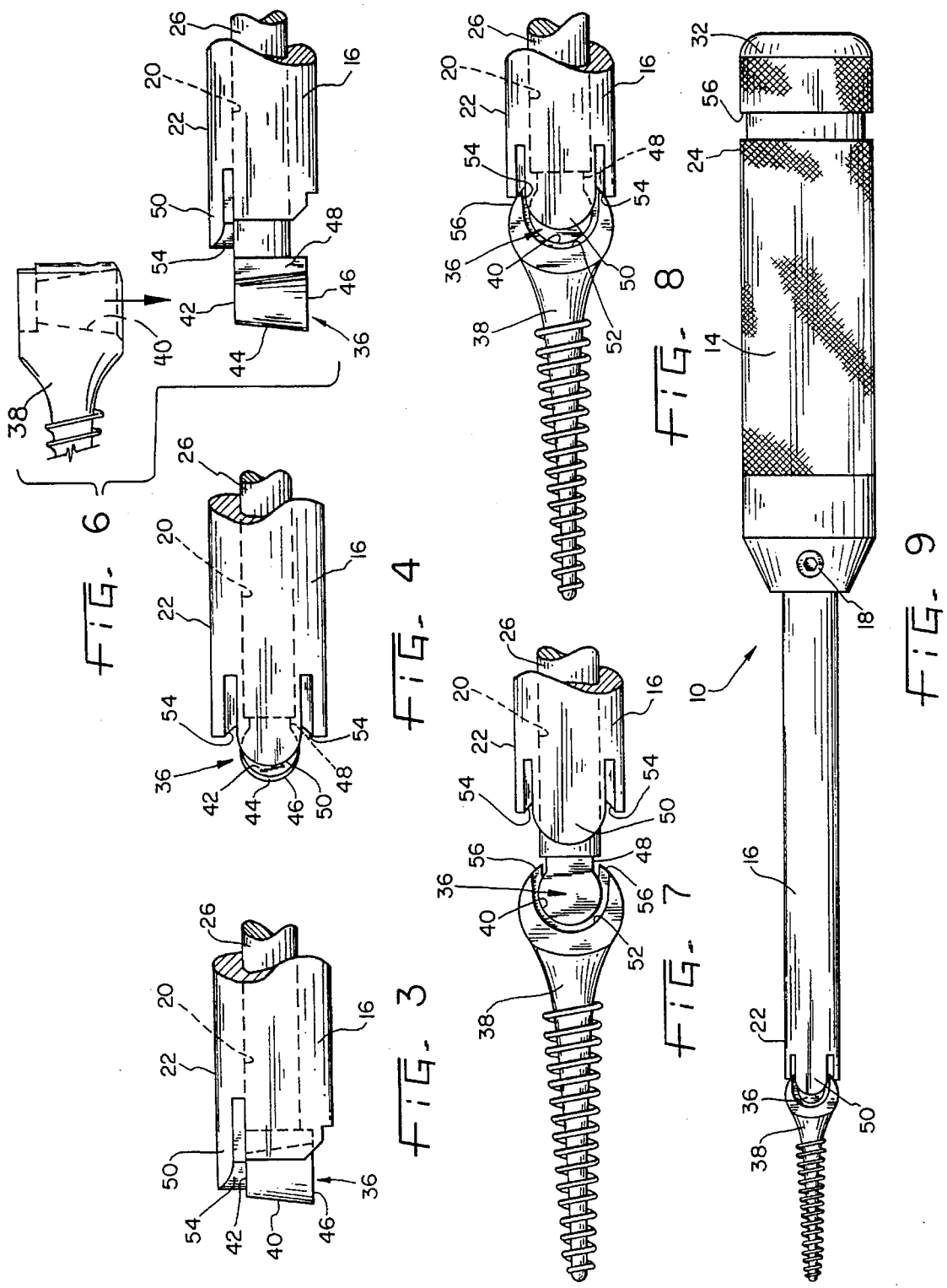

BONE SCREW AND SCREWDRIVER

This application is a continuation of application Ser. No. 07/970,908 filed Nov. 3, 1992, now abandoned.

BACKGROUND OF THE INVENTION

The present invention relates generally to bone screw screwdrivers and more particularly to a screwdriver that securely, positively locks the screw to the screwdriver.

The medical arts have advanced substantially in both design and materials. As is known in the orthopaedic field, various types of bone nails and screws are used for fixing implants and fractures where the fastener is attached to the bone. Bone screws may be implanted into the spine for stabilization in patients with spinal deformities and other injuries. Bone screws may hold rods which hold the back stiff while the vertebra are fused together. Thus, it is known to use bone screws for spinal fixation, as well as for other types of bone fixation or stabilization or to secure other implants. A high degree of precision is required to securely retain the devices in a proper working position.

Surgeons performing various orthopaedic operations work under difficult operating conditions. Not only must a surgeon focus his attention on the operating site and any complications which may arise, but the operating area is often not freely accessible. This often creates difficulty in fitting and positioning bone screws and/or other implants.

Normally during attachment of a bone screw, the surgeon requires one hand to expose tissue and hold the bone screw in position while the other hand rotatably drives the screw. In one current technique, bone screws are held by pliers in one hand of the surgeon while rotatably driven by a driver with the other hand. The non-positive lock between the pliers, screwdriver and bone screw make attachment of the screw more difficult, awkward and time consuming.

One screwdriver, as shown in U.S. Pat. No. 5,139,499, includes a radially compressible collet-like front portion that engages the axial bore of a screw. The front portion of the screwdriver deforms to create a spring bias to hold the screw to the driver. A possible problem is that the screw may not be fully engaged to the screwdriver. Furthermore, the material of the spring portion may fatigue or shear without notice during insertion of the screwdriver into the screw.

Another screwdriver, as shown in U.S. Pat. No. 4,963,144, has a longitudinal drive tube which is interfit with the threaded head of a bone screw. An associated jam rod is locked into place on the screw, to prevent its removal from the drive tube. A disadvantage of this system is the requirement for the head of the screw to include threads.

It is important that the screw does not disengage from the screwdriver when the screwdriver is driven into the bone. In areas of operation, such as the spinal column, a positive lock both axially and radially between the screw and screwdriver is important for proper placement of the bone screw. It is beneficial that the fastener used in a surgical procedure be retained by the driver so that the surgeon can positively position the fastener and rotatably drive it using one hand.

SUMMARY OF THE INVENTION

The present invention overcomes the disadvantages of the above described prior art by providing a screwdriver that securely and positively locks to a bone screw. The screwdriver yieldably interlocks with the bone screw before the positive lock is achieved.

In one form, the invention includes a tapered locking portion which slides into a partially enclosed groove in the bone screw to positively lock the screw to the screwdriver. The screwdriver can be easily disengaged after the screw is installed. The present invention works equally well on straight and angled bone screws.

In the preferred form of the invention, a sleeve is interfit with a slidable drive rod having, on the distal end, an attachment means. The attachment means includes a tapered locking portion which slides and interlocks into the partially enclosed groove in the bone screw. The locking portion operates much like the tongue in a tongue and groove mortise joint.

Another aspect of the invention is that of a spring which biases the locking portion of the drive rod into engagement with the distal end of the sleeve. This action causes the instrument to yieldably trap the bone screw between the locking tongue portion and sleeve. A tab located on the engaged distal end of the sleeve interfits with the screw and drive rod thereby preventing the drive rod and bone screw from rotating relative the sleeve.

An advantage of the bone screw screwdriver of the present invention, according to one form thereof, is that the bone screw is securely, positively locked to the screwdriver. When the screw in interlocked with the screwdriver, the surgeon is in control of the placement and orientation of the screw. The interlock between the screw and screwdriver permits proper placement and insertion of the bone screw into the patient.

Another advantage of the screwdriver of the present invention is that as soon as a bone screw is connected to the screwdriver, a spring biased clamping force biases the bone screw into an interlocked position. This clamping force automatically temporarily prevents the bone screw from disengaging from the screwdriver even before it is positively locked.

A further advantage of the screwdriver of the present invention is that both straight and angled screws may be rotationally driven with the same high degree of safety and control.

Yet a further advantage of the screwdriver of the present invention is that one handed driving of the bone screw is possible. Because the screw and screwdriver are interlocked together, a surgeon only needs to hold and rotate the screwdriver to drive the screw.

An additional advantage of the screwdriver is that not only is the bone screw locked rigidly, axially and radially, but also rotationally, relative to the screwdriver. By preventing relation rotation between the bone screw and screwdriver, a good "bite" by the bone screw into the bone tissue is assured.

The invention, in one form thereof, provides a bone screw screwdriver for driving a bone screw having a partially enclosed groove. The screwdriver includes a handle portion connected to a longitudinally extending sleeve having a bore therethrough. A drive rod is slidably disposed within the bore, with the rod distal end adjacent the sleeve's distal end. On the distal end of the drive rod is a tongue for attaching to the bone screw. The tongue is sized to interfit with and interlock to the partially enclosed groove. The screwdriver further includes a locking means for urging the sleeve distal end and the tongue together to clamp the screw therebetween.

In one aspect of the invention, the tongue interlocks with the bone screw. The tongue may be tapered thus having a narrow end and a wide end to slide into the bone screw, while the sleeve distal end includes a longitudinally extending tab which engages the bone screw over the tapered narrow end of the tongue acting as a stop to positively block the bone screw from disengaging from the tongue.

In another aspect of the previously described form of the invention, the locking means includes a spring chamber within the handle, oriented so that the drive rod is slidably disposed within the spring chamber. A control knob is threadably attached to the proximal end of the drive rod with the spring interfit about the drive rod, within the spring chamber, to yieldably bias the control knob away from the handle portion. This structure forces the tongue towards the sleeve distal end to yieldably lock a screw between the tongue and sleeve distal end. At times, the control knob is rotated about the drive rod into engagement with the handle portion, thereby positively locking the drive rod within the sleeve and positively locking the screw between the tongue and the sleeve distal end.

The invention, in another form thereof, provides a bone screw screwdriver for driving a bone screw with the screwdriver including a longitudinally extending drive rod attached to a handle, with a tongue means attached adjacent to the distal end of rod for interlocking with the partially enclosed groove. The tongue means interlocks with the bone screw in all but one direction. A selective stop means prevents the tongue means from unlocking from the bone screw in that one direction.

According to a further aspect of the invention, the bone screw screwdriver may include a longitudinally extending shank portion with a tongue portion attached to it's distal end, interlockable with the groove of the bone screw so that the bone screw is positively locked to the shank portion. An attachment means on the rod along with a interfitting sleeve may be used to clamp the bone screw to the screwdriver. A yieldable spring means urges the drive rod distal end toward the sleeve distal end to yieldably lock the screw between the drive rod and the sleeve thereby preventing accidental removal of the screw from the screwdriver.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is an exploded view of the bone screw screwdriver according to a preferred embodiment of the present invention;

FIG. 2 is a side view of the screwdriver;

FIG. 3 is an enlarged side view of the distal end of the screwdriver;

FIG. 4 is an enlarged top view of the distal end of the screwdriver;

FIG. 5 is a side view of the screwdriver with the drive rod extended;

FIG. 6 is an enlarged side view of the distal end of the screwdriver with the drive rod extended;

FIG. 7 is an enlarged top view of the distal end with the drive rod extended and engaging a bone screw;

FIG. 8 is an enlarged top view of the distal end shown with the bone screw interlocked therewith; and FIG. 9 is a top view of the screwdriver with an interlocked bone screw.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to FIGS. 1 and 2, there is shown the bone screw screwdriver 10 according to a preferred embodiment of the present invention. Screwdriver 10 includes, in a preferred embodiment, a knurled handle portion 14 and a shank portion 15 comprising a sleeve 16 connected to handle 14 by set screws 18. Sleeve 16 includes a distal end 22 while handle portion 14 includes a proximal end 24.

Sleeve 16 includes a bore 20 therethrough, as shown in FIG. 3, through which a drive rod 26 slidingly interfits. Handle portion 14 includes a spring chamber 27 through which drive rod 26 extends. The shank 15 also includes drive rod 26 having a distal end 28 and a proximal end 30.

As shown in FIG. 1, proximal end 30 of drive rod 26 is threaded so that it may threadably attach to a control knob 32 through a threaded hole (not shown). Control knob 32 slidably interfits within spring chamber 27 of handle portion 14. A yieldable biasing means such as spring 34 is interfit within spring chamber 27 about drive rod 26 to bias control knob 32 .away from handle portion 14.

Attachment means, such as a tongue 36, is located at distal end 28 of drive rod 26 to attach drive rod 26 to a screw 38. Tongue 36 interfits within an open-ended partially enclosed tapered groove 40 of screw 38 as shown in FIG. 7.

Tongue 36 interfits within groove 40 in such a way that it interlocks with screw 38 to prevent longitudinal separation. A preferred form of tongue 36 is that of a tapered cylinder tip as shown in FIG. 6. Tongue 36 includes a narrow top surface 42 and wider bottom surface 46 connected together by a tapered cylindrical surface 44. Tongue 36 is attached to drive rod 26 by a narrowed neck portion 48 as shown in FIGS. 4, 7 and 8. Narrowed neck portion 48, along with tapered cylindrical surface 44, permits tapered groove 40 of bone screw 38 to interlock around tongue 36, thereby interlocking screw 38 and drive rod 26 together. The narrowed neck portion 48 also helps prevent rotation of drive rod 26 with respect to the bore 20 of sleeve 16 when the narrowed neck portion is in contact with a corresponding inner edge (not shown) of sleeve 16,.such as in FIG. 3. Alternative attachment means may include other shapes for tongue 36 than shown in the drawings. The alternatives would comprise variations of a tongue and groove joint.

Partially enclosed groove 40 is correspondingly tapered to the shape of tongue 36 so that tongue 36 may interlock with groove 40 in all but one direction. In other words, tongue 36 and groove 40 are tapered such that tongue 36 may slide into groove 40 but is prevented from sliding all the way through groove 40. This structure prevents tongue 36 from sliding out of screw 38 except in the direction that the taper narrows (i.e. toward top surface 42 as viewed in FIG. 6).

To prevent rotation and positively lock bone screw 38 to tongue 36, a selectable stop means, such as a longitudinally extending tab 50, is integrally formed on distal end 22 of sleeve 16. As shown in FIG. 7, screw 38 includes a recessed, counterbored portion 52 about the periphery of partially enclosed groove 40. After the tongue 36 has been inserted into groove 40 while the drive rod 26 is in the extended position, when drive rod 26 and screw 38 are then moved axially toward sleeve 16, tab 50 slides over screw 38 and engages recessed portion 52 to act as a stop thereby preventing rotation of screw 38 and drive rod 26.

Further and more importantly, when tab 50 slides over screw 38 and narrow top portion 42 of tongue 36, screw 38 is positively locked on to tongue 36. Because tab 50 functions as a stop in the one direction in which screw 38 may slide off of tongue 36, (i.e. toward the top surface 42 of tongue 36), tab 50 prevents movement of bone screw 38 on tongue 36.

Biasing means, such as spring 34, is located within spring chamber 27 to prevent movement of bone screw 38 on tongue 36. Spring 34 creates a biasing force on control knob 32 which tends to axially push control knob 32 away from handle portion 14. Because drive rod 26 is threaded into control knob 32, the distal end 28 of drive rod 26 is retracted toward handle portion 14. Spring 34 urges drive rod distal end 28 to be pulled through sleeve 16. This action causes screw 38 to be yieldably biased directly against the inward sweeping front edges 54 of distal end 22, thereby yieldably locking screw 38 to sleeve 16. The sliding of screw 38 toward distal end 22 causes tab 50 to engage recess 52 of the screw as discussed above.

FIG. 4 shows distal end 22 of sleeve 16 including the inward sweeping front edges 54 that tongue 36 and screw 38 are at times biased against. Leading edge 56 of screw 38 engages the inward sweeping front edges 54 of distal end 22 when biased toward proximal end 24 of driver 10.

In operation, the bone screw screwdriver 10 of the present invention is utilized to positively lock and drive bone screws. First, control knob 32 is rotated, thereby becoming partially unthreaded from proximal end 30 of drive rod 26 (FIG. 2). Control knob 32 is unthreaded far enough so that when pushed axially toward distal end 22 (FIG. 5), drive rod 26 is pushed axially forward far enough so that screw 38 may be interfit on tongue 36. Partially enclosed groove 40 of bone screw 38 is then slid and interfit on tapered surface 44 of tongue 36 (FIG. 7).

After screw 38 is attached, control knob 32 is released, permitting spring 34 to move control knob 32 axially away from handle 14 (FIG. 9). Spring 34 urges attached screw 38 into engagement with front edges 54 of distal end 22. At the same time, movement of screw 38 urges recess 52 into engagement with tab 50.

At this time, screw 38 is yieldably locked to screwdriver 10 by spring 34 and the interlock mechanism of distal end 22. When control knob 32 is released as stated before, it moves axially away from handle portion 14 (FIG. 9). With screw 38 interlocked with distal end 22 and tab 50, control knob 32 is screwed into handle portion 14. As control knob 32 threadably rotates upon proximal end 30 of drive rod 26, shoulder 56 of control knob 32 is urged closer and closer to distal end 24 of handle portion 14, until shoulder 56 engages distal end 24. Control knob 32 thus acts as a locking means. Screwdriver 10 has now completely, positively locked screw 38 to distal end 22 (FIG. 8). At this time, drive rod 26 is not axially movable within sleeve 16 because of interlocked screw 38 on distal end 28 and threaded control knob 32 on proximal end 30 in its locked position.

After these steps have been completed, screwdriver 10 may be used to rotationally drive screw 38 in a known fashion.

When screw 38 is installed, the surgeon will reverse the steps to release screwdriver 10 from screw 38. First control knob 32 is partially unthreaded from proximal end 30, thereby permitting shoulder 56 to disengage from handle portion 14. After this is accomplished, force is applied to control knob 32 to counteract the bias force of spring 34 and thereby extend the drive rod 26 to release tab 50 from recessed portion 52.

At this time, screw 38 is engaged only by tongue 36 and tapered surface 44. Tongue 36 is then slid out from groove 40, thereby releasing screwdriver 10 from screw 38.

It is noted that when the screwdriver of this invention is used with an angled screw, not shown, the tongue 36 of the screwdriver may be oriented with respect to the drive rod 26 at an angle different from that shown in the Figs., so that the axis of the threaded portion of the angled screw is aligned with the axis of the screwdriver. Such alignment facilitates insertion of the angled screw. Angled screws, as known in the art, typically provide a screw in which the threaded portion of the screw is angled with respect to the screw head.

The description above relates to using instrument 10 to drive a bone screw 38, but driver 10 may also be used to provide a positive interlock in connection with other prosthetic devices or surgical instruments. The function of tongue 36 permits interconnection and interlocking with any such member having a corresponding groove thereon.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. In combination, a bone screw and a bone screw screwdriver for driving said bone screw, said bone screw having a partially enclosed tapered groove, said screwdriver comprising:

a handle portion;

a longitudinally extending sleeve connected to said handle portion and having a bore therethrough, said sleeve having a distal end;

a drive rod slidably disposed within said bore, said rod having a proximal end and a distal end and a longitudinal axis, said rod distal end being located adjacent said sleeve distal end;

a tapered tongue on said distal end of said drive rod for attaching the bone screw to said drive rod, said tapered tongue sized to interfit within and interlock to said partially enclosed tapered groove; and locking means for urging said sleeve distal end and said tongue together to thereby clamp the screw therebetween, in which said locking means further includes a resilient biasing means for resiliently retracting and biasing said drive rod distal end toward said sleeve distal end to retain the bone screw on said tongue, and wherein the biasing means enables the tongue on the drive rod to be selectively extended from the sleeve distal end to enable the bone screw to be attached to the tongue, and wherein said tapered tongue positively interlocks with the tapered groove in the bone screw in all but one direction while the tongue is extended from the sleeve distal end, and wherein said one direction is transverse to the longitudinal axis of the drive rod, and wherein the taper of said tongue has a narrow end and a wide end, said sleeve distal end includes a longitudinally extending tab which engages the bone screw over said tapered narrow end of said tongue to act as a stop and positively block the bone screw from disengaging from said tongue when the drive rod distal end is retracted.

2. In combination, a bone screw and a bone screw screwdriver for driving said bone screw, said bone screw having a partially enclosed groove, said screwdriver comprising:

a handle portion;

a longitudinally extending sleeve rigidly connected to said handle portion and having a bore therethrough, said sleeve having a distal end;

a drive rod slidably disposed within said bore, said rod having a proximal end and a distal end and a longitudinal axis, said rod distal end being located adjacent said sleeve distal end;

a tongue on said distal end of said drive rod for attaching the bone screw to said drive rod, said tongue sized to interfit within and interlock to said partially enclosed groove, and wherein said tongue is a cylinder having a longitudinal axis which is transverse to the longitudinal axis of said drive rod; and locking means for urging said sleeve distal end and said tongue together to thereby clamp the screw therebetween, in which said locking means comprises a spring chamber within said handle portion, said drive rod also slidably disposed within said spring chamber, a control knob threadably attached to said proximal end of said drive rod, a spring interfit about said drive rod within said spring chamber to yieldably bias said control knob and proximal end of said drive rod away from said handle portion, thereby forcing said tongue toward said sleeve distal end to yieldably lock the screw between said tongue and sleeve distal end and enabling the control knob and drive rod to be selectively manually pushed toward the handle portion against the spring to force the drive rod through the sleeve to position the tongue away from the sleeve distal end.

3. The screwdriver of claim 2 in which said control knob is rotatable about said drive rod into engagement with said handle portion thereby positively locking said drive rod relative to said sleeve and positively locking the screw between said tongue and said sleeve distal end.

4. The method of securing a bone screw having a head which includes a partially enclosed groove to interfit with a screwdriver, the method comprising:

providing a screwdriver having a handle portion with a longitudinally extending sleeve rigidly connected thereto, with a slidable drive rod disposed through said sleeve and said handle portion, said drive rod having a tongue on a distal end to interfit within the groove of the bone screw, said drive rod including an axial spring means about said drive rod within a spring chamber in the handle portion to urge said tongue toward a distal end of said sleeve, said screwdriver having a rotatable control knob that selectively locks said drive rod relative to said sleeve and wherein the spring means yieldably biases said control knob and a proximal end of said drive rod away from said handle portion;

pushing said control knob toward said handle portion and thereby forcing said drive rod through said sleeve to position said tongue away from said sleeve so as to permit connection of said tongue with the bone screw;

interfitting said tongue into the groove in the bone screw so that the bone screw is attached to said screwdriver;

releasing said control knob thereby allowing said spring means to move said drive rod within said sleeve and clamp the screw between said drive rod and said sleeve;

rotating said control knob to lock said drive rod relative to said sleeve;

rotating said screwdriver and driving said bone screw into a bone;

reverse rotating said control knob to unlock said drive rod relative to said sleeve;

pushing said control knob toward said handle portion and thereby forcing said drive rod through said sleeve to release the screw from grasp of said drive rod and said sleeve; and detaching said tongue from the screw.

* * * * *